United States Patent
Bando et al.

(10) Patent No.: US 11,802,119 B2
(45) Date of Patent: Oct. 31, 2023

(54) METHOD FOR PRODUCING CYCLIC DISULFONIC ACID ESTER COMPOUND

(71) Applicant: SUMITOMO SEIKA CHEMICALS CO., LTD., Hyogo (JP)

(72) Inventors: Seiji Bando, Hyogo (JP); Hirotake Moriyama, Hyogo (JP); Seiya Ashibe, Hyogo (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 121 days.

(21) Appl. No.: 17/629,186

(22) PCT Filed: Jul. 22, 2020

(86) PCT No.: PCT/JP2020/028367
§ 371 (c)(1),
(2) Date: Jan. 21, 2022

(87) PCT Pub. No.: WO2021/015220
PCT Pub. Date: Jan. 28, 2021

(65) Prior Publication Data
US 2022/0251060 A1    Aug. 11, 2022

(30) Foreign Application Priority Data

Jul. 23, 2019  (JP) ................. 2019-135410

(51) Int. Cl.
*C07D 327/00* (2006.01)
*C07D 327/10* (2006.01)

(52) U.S. Cl.
CPC ......... *C07D 327/10* (2013.01); *C07D 327/00* (2013.01)

(58) Field of Classification Search
CPC ..................... C07D 327/00; C07D 327/10
See application file for complete search history.

(56) References Cited

U.S. PATENT DOCUMENTS

| | | | |
|---|---|---|---|
| 2009/0137820 A1 | 5/2009 | Hiyama et al. | |
| 2013/0137881 A1 | 5/2013 | Bando et al. | |

FOREIGN PATENT DOCUMENTS

| | | |
|---|---|---|
| CN | 102344436 A | 2/2012 |
| IN | 2018-21043808 A | 7/2019 |
| JP | S61-501089 A | 5/1986 |
| JP | H05-44946 B2 | 7/1993 |
| JP | 2005-336155 A | 12/2005 |
| KR | 10-2019-0003015 A | 1/2019 |
| WO | 85/03075 A1 | 7/1985 |
| WO | 2007/125736 A1 | 11/2007 |
| WO | 2012/026266 A1 | 3/2012 |

OTHER PUBLICATIONS

Akira Yanagase, et al., "Kinetic Study on the Synthesis of Methyl Glycolate from Methylene Sulfate and Carbon-Monoxide under Pressure", Nippon Kagaku Kaishi, vol. 4, 1975, pp. 583-590.
International Search Report for PCT/JP2020/028367 dated Sep. 29, 2020 (PCT/ISA/210).

*Primary Examiner* — Laura L Stockton
(74) *Attorney, Agent, or Firm* — Sughrue Mion, PLLC

(57) ABSTRACT

Provided is a novel production method capable of easily producing a cyclic disulfonic acid ester compound. This method for producing a cyclic disulfonic acid ester compound comprises reacting a specific sulfonic acid compound with a specific sulfuric acid ester compound.

4 Claims, No Drawings

METHOD FOR PRODUCING CYCLIC DISULFONIC ACID ESTER COMPOUND

CROSS REFERENCE TO RELATED APPLICATIONS

This application is a National Stage of International Application No. PCT/JP2020/028367 filed Jul. 22, 2020, claiming priority based on Japanese Patent Application No. 2019-135410 filed Jul. 23, 2019.

TECHNICAL FIELD

The present disclosure relates to a method for producing a cyclic disulfonic acid ester compound and the like. The contents of all of the documents described in the present specification are incorporated herein by reference.

BACKGROUND ART

Cyclic disulfonic acid ester compounds are useful as intermediates of pharmaceuticals and agrochemicals, and functional materials. Methylene disulfonate compounds are known to be useful in pharmaceutical products such as animal leukemia drugs; stabilizers for secondary battery electrodes; and the like.

For example, Patent Literature (PTL) 1 discloses a method for producing a methylene disulfonate compound by reacting silver disulfonate, which is obtained by reacting disulfonyl chloride with silver carbonate, with diiodomethane.

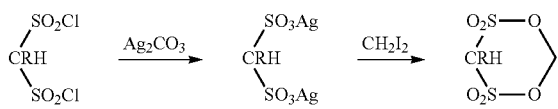

Further, for example, Patent Literature (PTL) 2 discloses a method for producing a methylene disulfonate compound by reacting an alkane disulfonic acid or the like with methylene diacetate or the like.

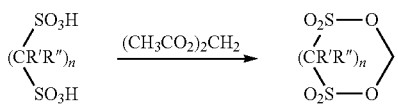

Further, for example, Patent Literature (PTL) 3 discloses a method for producing a methylene disulfonate compound by converting methanedisulfonic acid to methanedisulfonic acid chloride using a chlorinating agent such as thionyl chloride and then reacting the methanedisulfonic acid chloride with formaldehyde.

Further, for example, Patent Literature (PTL) 4 discloses a method for producing a cyclic disulfonic acid ester compound by reacting silver disulfonate, which is obtained by reacting disulfonyl chloride with silver carbonate, with 1,2-dibromoethane or 1,4-dibromobutane.

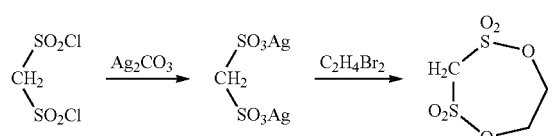

CITATION LIST

Patent Literature

PTL 1: JPS61-501089A
PTL 2: JP2005-336155A
PTL 3: CN102344436A
PTL 4: JPHS-44946B

SUMMARY OF INVENTION

Technical Problem

However, the method of Patent Literature (PTL) 1 has problems such that in addition to the method using expensive silver carbonate and diiodomethane, the reaction proceeds slowly, and the desired product may not be obtained with a satisfactory yield; furthermore, since a stoichiometric amount of poorly soluble silver iodide is produced as a byproduct, handleability in transfer and filtration processes may become a problem.

The method of Patent Literature (PTL) 2 has a problem such that the methylene diacetate to be used is difficult to obtain and expensive.

The method of Patent Literature (PTL) 3 has problems such that in addition to the method comprising a complicated production process, which is a multi-step reaction process, a chlorinating agent causes a side reaction that produces a toxic by-product.

The method of Patent Literature (PTL) 4 also has problems such that in addition to the method using expensive silver carbonate, the reaction proceeds slowly and the desired product may not be obtained with a satisfactory yield; furthermore, since a stoichiometric amount of poorly soluble silver bromide is produced as a byproduct, handleability in transfer and filtration processes may become a problem.

As described above, none of the previously known methods can be considered to always be satisfactory production methods for industrial-scale mass production.

The present inventors conducted research in order to provide a novel production method capable of easily producing a cyclic disulfonic acid ester compound. Specifically, the inventors found the possibility that a cyclic disulfonic acid ester compound could be easily produced by reacting a specific sulfonic acid compound with a specific sulfuric acid ester compound, and made further improvements.

The present disclosure encompasses, for example, the subjects described in the following items.

Item 1

A method for producing a cyclic disulfonic acid ester compound, the method comprising reacting at least one sulfonic acid compound with at least one sulfuric acid ester compound, the sulfonic acid compound being selected from the group consisting of:

compounds represented by formula (1):

(wherein two Xs are the same or different and represent a hydrogen atom or an alkali metal;
$R^1$ and $R^2$ are the same or different and represent a $C_{1-4}$ alkyl group optionally substituted with one or more halogen atoms or a hydrogen atom;
n1 is an integer of 1 to 4;
when n1 is an integer of 2 to 4, n1 R's may be the same or different and n1 $R^2$s may be the same or different); and
compounds represented by formula (2):

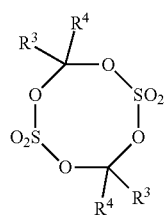
(2)

(wherein Y represents an alkaline earth metal, and $R^1$, $R^2$, and n1 are as defined above), and
the sulfuric acid ester compound being selected from the group consisting of:
compounds represented by formula (3):

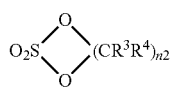
(3)

(wherein $R^3$ and $R^4$ are the same or different and represent a $C_{1-4}$ alkyl group optionally substituted with one or more halogen atoms or a hydrogen atom); and
compounds represented by formula (4):

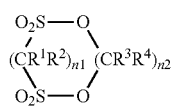
(4)

(wherein n2 is an integer of 1 to 4, and
$R^3$ and $R^4$ are as defined above), and
the cyclic disulfonic acid ester compound being represented by formula (5):

$$\begin{array}{c} O_2S-O \\ (CR^1R^2)_{n1} \; (CR^3R^4)_{n2} \\ O_2S-O \end{array}$$
(5)

(wherein $R^1$, $R^2$, $R^3$, $R^4$, n1, and n2 are as defined above).
Item 2
The method for producing a cyclic disulfonic acid ester compound according to Item 1, wherein the sulfuric acid ester compound is at least one sulfuric ester compound selected from the group consisting of the compounds represented by formula (3) and the compounds represented by formula (4) wherein n2 is 1.

Item 3
The method for producing a cyclic disulfonic acid ester compound according to Item 1 or 2, wherein the sulfonic acid compound is a compound of formula (1) wherein two Xs are both a hydrogen atom.

Advantageous Effects of Invention

A production method that enables easy and inexpensive production of a cyclic disulfonic acid ester compound is provided. This production method is industrially advantageous because the viscosity of the reaction mixture during the production process is relatively low and the reaction mixture exhibits good handleability even in industrial-scale production.

DESCRIPTION OF EMBODIMENTS

Embodiments included in the present disclosure are described in more detail below. The present disclosure preferably includes a method for producing a cyclic disulfonic acid ester compound etc., but is not limited thereto. The present disclosure includes everything that is disclosed in the present specification and recognizable to those skilled in the art.

The method for producing a cyclic disulfonic acid ester compound included in the present disclosure comprises reacting a specific sulfonic acid compound with a specific sulfuric acid ester compound.

The specific sulfonic acid compound is at least one member selected from the group consisting of compounds represented by formula (1) and compounds represented by formula (2).

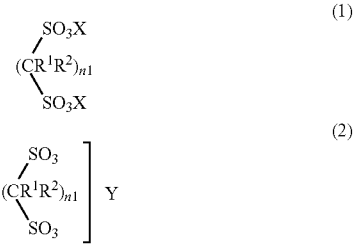

In formulas (1) and (2), $R^1$ and $R^2$ independently (i.e., may be the same or different) represent a $C_{1-4}$ ($C_1$, $C_2$, $C_3$, or $C_4$) alkyl group optionally substituted with one or more halogen atoms or a hydrogen atom, and n1 is an integer of 1 to 4 (1, 2, 3, or 4). Xs are the same or different (preferably the same) and represent a hydrogen atom or an alkali metal, and Y represents an alkaline earth metal.

Examples of halogen atoms in the $C_{1-4}$ alkyl group optionally substituted with one or more halogen atoms include a fluorine atom, a chlorine atom, a bromine atom, and the like. Specific examples of the $C_{1-4}$ alkyl group optionally substituted with one or more halogen atoms include methyl, ethyl, n-propyl, iso-propyl, n-butyl, iso-butyl, sec-butyl, tert-butyl, fluoromethyl, trifluoromethyl, chloromethyl, chloroethyl, chloropropyl, bromomethyl, and the like.

$R^1$ and $R^2$ preferably represent a hydrogen atom, methyl, ethyl, and n-propyl, and more preferably a hydrogen atom.

In formula (1) and formula (2), when n1 is an integer of 2 to 4 (2, 3, or 4), n1 $R^1$s may be the same or different, and n1 $R^2$s may be the same or different; and n1 is preferably 1.

Examples of alkali metals represented by X include lithium, sodium, potassium, and the like.

Examples of alkaline earth metals represented by Y include magnesium, calcium, barium, and the like.

The sulfonic acid compound used in the present invention is preferably a compound of formula (1) wherein two Xs are the same or different and represent a hydrogen atom, sodium, or potassium, and more preferably a compound of formula (1) wherein two Xs are a hydrogen atom.

Specific examples of sulfonic acid compounds represented by formula (1) include the following compounds.

Methanedisulfonic acid (X=H, $R^1=R^2$=H, n=1), 1,1-ethanedisulfonic acid (X=H, $R^1$=$CH_3$, $R^2$=H, n=1), 1,2-ethanedisulfonic acid (X=H, $R^1=R^2$=H, n=2), 1,1-propanedisulfonic acid (X=H, $R^1$=$CH_2CH_3$, $R^2$=H, n=1), 1,2-propanedisulfonic acid (X=H, $R^1$=$CH_3$ and H, $R^2$=H, n=2), 1,3-propanedisulfonic acid (X=H, $R^1=R^2$=H, n=3), 2,2-propanedisulfonic acid (X=H, $R^1=R^2$=$CH_3$, n=1), 1,4-butanedisulfonic acid (X=H, $R^1=R^2$=H, n=4), sodium methanedisulfonate (X=Na, $R^1=R^2$=H, n=1), sodium 1,1-ethanedisulfonate (X=Na, $R^1$=$CH_3$, $R^2$=H, n=1), sodium 1,2-ethanedisulfonate (X=Na, $R^1=R^2$=H, n=2), sodium 1,1-propanedisulfonate (X=Na, $R^1$=$CH_2CH_3$, $R^2$=H, n=1), sodium 1,2-propanedisulfonate (X=Na, $R^1$=$CH_3$ and H, $R^2$=H, n=2), sodium 1,3-propanedisulfonate (X=Na, $R^1=R^2$=H, n=3), sodium 2,2-propanedisulfonate (X=Na, $R^1=R^2$=$CH_3$, n=1), sodium 1,4-butanedisulfonate (X=Na, $R^1=R^2$=H, n=4), potassium methanedisulfonate (X=K, $R^1=R^2$=H, n=1), potassium 1,1-ethanedisulfonate (X=K, $R^1$=$CH_3$, $R^2$=H, n=1), potassium 1,2-ethanedisulfonate (X=K, $R^1=R^2$=H, n=2), potassium 1,1-propanedisulfonate (X=K, $R^1$=$CH_2CH_3$, $R^2$=H, n=1), potassium 1,2-propanedisulfonate (X=K, $R^1$=$CH_3$ and H, $R^2$=H, n=2), potassium 1,3-propanedisulfonate (X=K, $R^1=R^2$=H, n=3), potassium 2,2-propanedisulfonate (X=K, $R^1=R^2$=$CH_3$, n=1), and potassium 1,4-butanedisulfonate (X=K, $R^1=R^2$=H, n=4).

Specific examples of sulfonic acid compounds represented by formula (2) include the following compounds.

Calcium methanedisulfonate (Y=Ca, $R^1=R^2$=H, n=1), calcium 1,2-ethanedisulfonate (Y=Ca, $R^1=R^2$=H, n=2), magnesium methanedisulfonate (Y=Mg, $R^1=R^2$=H, n=1), barium methanedisulfonate (Y=Ba, $R^1=R^2$=H, n=1), barium 1,2-ethanedisulfonate (Y=Ba, $R^1=R^2$=H, n=2), barium 1,2-propanedisulfonate (Y=Ba, $R^1$=$CH_3$ and H, $R^2$=H, n=2), barium 1,3-propanedisulfonate (Y=Ba, $R^1=R^2$=H, n=3), barium 1,4-butanedisulfonate (Y=Ba, $R^1=R^2$=H, n=4).

The sulfonic acid compound may be a commercially available product, or may be prepared by a known method or a method readily conceivable from known methods. For example, the sulfonic acid compound can be prepared by a method comprising reacting the corresponding disulfonyl halide with water with reference to JP2005-336155A. Alternatively, the sulfonic acid compound can also be prepared by reacting dichloromethane with an alkali salt of sulfurous acid in an aqueous solvent at 150 to 160° C. with reference to Recueil des Travaux Chimiques des Pays-Bas, 48, 949-952 (1929).

Such sulfonic acid compounds can be used singly or in a combination of two or more.

The specific sulfuric acid ester compound is at least one member selected from the group consisting of compounds represented by formula (3) and compounds represented by formula (4).

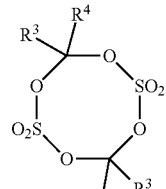

(3)

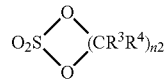

(4)

In each of formulas (3) and (4), $R^3$ and $R^4$ independently (i.e., may be the same or different) represent a $C_{1-4}$ alkyl group optionally substituted with one or more halogen atoms or a hydrogen atom.

As described above, examples of halogen atoms in the $C_{1-4}$ alkyl group optionally substituted with one or more halogen atoms include a fluorine atom, a chlorine atom, a bromine atom, and the like. Specific examples of the $C_{1-4}$ alkyl group optionally substituted with one or more halogen atoms include methyl, ethyl, n-propyl, iso-propyl, n-butyl, iso-butyl, sec-butyl, tert-butyl, fluoromethyl, trifluoromethyl, chloromethyl, chloroethyl, chloropropyl, bromomethyl, and the like.

$R^3$ and $R^4$ preferably represent a hydrogen atom, methyl, ethyl, and n-propyl, and more preferably a hydrogen atom.

In formula (3), two $R^3$s may be the same or different, and two $R^4$s may be the same or different.

In formula (4), n2 is an integer of 1 to 4 (1, 2, 3, or 4). When n2 is an integer of 2 to 4, n2 $R^3$s may be the same or different, and n2 $R^4$s may be the same or different. n2 is preferably 1.

The specific sulfuric acid ester compound can be synthesized, for example, by known methods or by methods easily conceivable from known methods.

For example, with reference to the Journal of Chemical Society, 1765-1771 (1931) and the Journal of Chemical Society, 86-91 (1932), the sulfuric acid ester compound can be synthesized by a method comprising adding paraformaldehyde to 50% fuming sulfuric acid (concentrated sulfuric acid containing 50 mass % sulfur trioxide) and allowing the reaction to proceed at 60 to 70° C. or by a method comprising reacting the corresponding dibromoalkylene with silver sulfate. Further, for example, with reference to JPH05-507936B, the sulfuric acid ester compound can be synthesized by a method comprising reacting sulfur trioxide with the corresponding alkylene oxide in a dioxane solvent at 45° C.

The specific sulfuric acid ester compound can be used singly or in a combination of two or more.

A cyclic disulfonic acid ester compound represented by formula (5) (wherein $R^1$, $R^2$, $R^3$, $R^4$, n1, and n2 are as defined above) can be produced by reacting the specific sulfonic acid compound and the specific sulfuric acid ester compound described above.

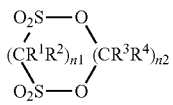

(5)

The amount of the sulfuric acid ester compound to be used can be, for example, 0.3 to 10 moles, preferably 0.6 to 5.0 moles, per 1.0 mole of the sulfonic acid compound.

In particular, when the sulfuric acid ester compound is a compound represented by formula (3), the amount of the sulfonic acid compound can be, for example, 0.30 to 5.0 moles, preferably 0.35 to 4.0 moles, and more preferably 0.4 to 3.0 moles, per 1.0 mole of the sulfonic acid compound.

In particular, when the sulfuric acid ester compound is a compound represented by formula (4), the amount of the sulfonic acid compound can be, for example, 0.6 to 10 moles, preferably 0.7 to 7.0 moles, and more preferably 0.8 to 5.0 moles, per 1.0 mole of the sulfonic acid compound.

In the above reaction, a solvent may be used as necessary. The amount of the solvent used can be, for example, 0 to 1500 parts by mass, and preferably 0 to 1000 parts by mass, per 100 parts by mass of the sulfonic acid compound. The lower limit of the range of the amount of the solvent is not limited, but can be, for example, about 1, 5, or 10 parts by mass.

Examples of solvents include hydrocarbon solvents, ether solvents, ketone solvents, ester solvents, amide solvents, nitrile solvents, sulfoxide solvents, sulfone solvents, sulfuric acid, and the like. Examples of hydrocarbon solvents include toluene, xylene, monochlorobenzene, dichlorobenzene, trichlorobenzene, hexane, heptane, decane, and the like. Examples of ether solvents include diethyl ether, ethylene glycol dimethyl ether, diisopropyl ether, diphenyl ether, tetrahydrofuran, dioxane, methyl-tert-butyl ether, cyclopentyl methyl ether, and the like. Examples of ketone solvents include acetone, methyl ethyl ketone, methyl isobutyl ketone, and the like. Examples of ester solvents include ethyl acetate, butyl acetate, and the like. Examples of amide solvents include dimethylformamide, dimethylacetamide, N-methylpyrrolidone, and the like. Examples of nitrile solvents include acetonitrile and the like. Examples of sulfoxide solvents include dimethylsulfoxide and the like. Examples of sulfonic solvents include ethylmethylsulfone, ethylisopropylsulfone, sulfolane, 3-methylsulfolane, and the like.

Among them, preferable solvents are ether solvents, ketone solvents, ester solvents, amide solvents, nitrile solvents, sulfoxide solvents, sulfone solvents, and sulfuric acid; more preferably sulfoxide solvents, sulfone solvents, and sulfuric acid; and even more preferably sulfoxide solvents and sulfone solvents.

In the production of a cyclic disulfonic acid ester compound, as long as a sulfonic acid compound is reacted with a sulfuric ester compound, the reaction method is not particularly limited. Examples of reaction methods include a method comprising placing a sulfuric acid ester compound, which is prepared beforehand by synthesis and isolation with reference to the above literature, and a sulfonic acid compound in a reaction vessel and allowing the reaction of the sulfonic acid compound with the sulfuric acid ester compound to proceed; a method comprising synthesizing a sulfuric acid ester compound in a reaction vessel and adding a sulfonic acid compound to the reaction mixture without isolating the obtained sulfuric acid ester compound to allow the reaction of the sulfonic acid compound with the sulfuric acid ester compound to proceed; and the like.

The reaction temperature is usually 0 to 200° C., and is preferably 10 to 150° C.

The reaction time may vary depending on the reaction temperature; however, it is usually 0.1 to 20 hours, and preferably 1 to 12 hours.

The method can produce a cyclic disulfonic acid ester compound represented by formula (5):

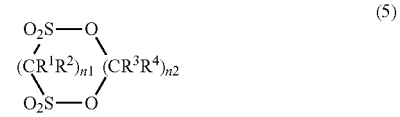

(5)

(wherein $R^1$, $R^2$, $R^3$, $R^4$, n1, and n2 are the same as defined above).

Specific examples of cyclic disulfonic acid ester compounds represented by formula (5) include methylene methanedisulfonate ($R^1=R^2=H$, $R^3=R^4=H$, n1=1, n2=1) methylene-1,1-ethanedisulfonate ($R^1=CH_3$, $R^2=H$, $R^3=R^4=H$, n1=1, n2=1) methylene-1,2-ethanedisulfonate ($R^1=R^2=H$, $R^3=R^4=H$, n1=2, n2=1), methylene-1,1-propanedisulfonate ($R^1=CH_2CH_3$, $R^2=H$, $R^3=R^4=H$, n1=1, n2=1) methylene-1,2-propanedisulfonate ($R^1=CH_3$ and H, $R^2=H$, $R^3=R^4=H$, n1=2, n2=1), methylene-1,3-propanedisulfonate-1,3-propanedisulsonate ($R^1=R^2=H$, $R^3=R^4=H$, n1=3, n2=1) methylene-2,2-propanedisulfonate ($R^1=CH_3$, $R^2=CH_3$, $R^3=R^4=H$, n1=1, n2=1), methylene-1,4-butanedisulfonate ($R^1=R^2=H$, $R^3=R^4=H$, n1=4, n2=1), 1,2-ethylene methanedisulfonate ($R^1=R^2=H$, $R^3=R^4=H$, n1=1, n2=2) 1,2-ethylene-1,1-ethanedisulfonate ($R^1=CH_3$, $R^2=H$, $R^3=R^4=H$, n1=1, n2=2), 1,2-ethylene-1,2-ethanedisulfonate ($R^1=R^2=H$, $R^3=R^4=H$, n1=2, n2=2), 1,2-ethylene-1,1-propanedisulfonate ($R^1=CH_2CH_3$, $R^2=H$, $R^3=R^4=H$, n1=1, n2=2), 1,2-ethylene-1,2-propanedisulfonate ($R^1=CH_3$ and H, $R^2=H$, $R^3=R^4=H$, n1=2, n2=2), 1,2-ethylene-1,3-propanedisulfonate ($R^1=R^2=H$, $R^3=R^4=H$, n1=3, n2=2), 1,2-ethylene-2,2-propanedisulfonate ($R^1=CH_3$, $R^2=CH_3$, $R^3=R^4=H$, n1=1, n2=2) 1,2-ethylene-1,4-butanedisulfonate ($R^1=R^2=H$, $R^3=R$ 4=H, n1=4, n2=2), 1,1-ethylene methanedisulfonate ($R^1=R^2=H$, $R^3=CH_3$, $R^4=H$, n1=1, n2=1), 1,1-ethylene-1,1-ethanedisulfonate ($R^1=CH_3$, $R^2=H$, $R^3=CH_3$, $R^4=H$, n1=1, n2=1), 1,1-ethylene-1,2-ethanedisulfonate ($R^1=R^2=H$, $R^3=CH_3$, $R^4=H$, n1=2, n1) 1,1-ethylene-1,1-propanedisulfonate ($R^1=CH_2CH_3$, $R^2=H$, $R^3=CH_3$, $R^4=H$, n1=1, n2=1) 1,1-ethylene-1,2-propanedisulfonate ($R^1=CH_3$ and H, $R^2=H$, $R^3=CH_3$, $R^4=H$, n1=2, n2=1) 1,1-ethylene-1,3-propanedisulfonate ($R^1=R^2=H$, $R^3=CH_3$, $R^4=H$, n1=3, n2=1), 1,1-ethylene-2,2-propanedisulfonate ($R^1=CH_3$, $R^2=CH_3$, $R^3=CH_3$, $R^4=H$ n1=1, n2=1), 1,1-ethylene-1,4-butanedisulfonate ($R^1=R^2=H$, $R^3=CH_3$, $R^4=H$, n1=4, n2=1), 1,3-propylenemethanedisulfonate ($R^1=R^2=H$, $R^3=R^4=H$, n1=1, n2=3), 1,3-propylene-1,1-ethanedisulfonate ($R^1=CH_3$, $R^2=H$, $R^3=R^4=H$, n1=1, n 2=3), 1,3-propylene-1,2-ethanedisulfonate ($R^1=R^2=H$, $R^3=R^4=H$, n1=2, n2=3), 1,3-propylene-1,1-propanedisulfonate ($R^1=CH_2CH_3$, $R^2=H$, $R^3=R^4=H$, n1=1, n2=3), 1,3-propylene-1,2-propanedisulfonate ($R^1=CH_3$ and H, $R^2=H$, $R^3=R^4=H$, n1=2, n2=3), 1,3-propylene-1,3-propanedisulfonate ($R^1=R^2=H$, $R^3=R^4=H$, n1=3, n2=3), 1,3-propylene-2,2-propanedisulfonate ($R^1=CH_3$, $R^2=CH_3$, $R^3=R^4=H$, n1=1, n2=3), 1,3-propylene-1,4-butanedisulfonate ($R^1=R^2=H$, $R^3=R^4=H$, n1=4, n2=3), 1,2-propylenemethanedisulfonate ($R^1=R^2=H$, $R^3=CH_3$ and H, $R^4=H$, n1=1, n2=2), 1,2-propylene-1,1-ethanedisulfonate ($R^1=CH_3$, $R^2=H$, $R^3=CH_3$ and H, $R^4=H$, n1=1, n2=2), 1,2-propylene-1,2-ethanedisulfonate ($R^1=R^2=H$, $R^3=CH_3$ and H, $R^4=H$, n1=2, n2=2), 1,2-propylene-1,1-propanedisulfonate ($R^1=CH_2CH_3$, $R^2=H$, $R^3=CH_3$ and H, $R^4=H$, n1=1, n2=2), 1,2-propylene-1,2-propanedisulfonate ($R^1$=CH$_3$ and H, $R^2$=H, $R^3$=CH$_3$ and H, $R^4$=H, n1=2, n2=2), 1,2-propylene-1,3-propanedisulfonate ($R^1$=$R^2$=H, $R^3$=CH$_3$ and H, $R^4$=H, n1=3, n2=2), 1,2-propylene-2,2-propanedisulfonate ($R^1$=CH$_3$, $R^2$=CH$_3$, $R^3$=CH$_3$ and H, $R^4$=H, n1=1, n2=2), 1,2-propylene-1,4-butanedisulfonate ($R^1$=$R^2$=H, $R^3$=CH$_3$ and H, $R^4$=H, n1=4, n2=2), and the like.

The methylene disulfonate compound obtained by the above method can be isolated, for example, by conventional known purification and isolation operations. The method for purification and isolation is not particularly limited. Examples of usable methods include a method comprising subjecting the reaction mixture to extraction using a solvent or the like, then washing with water or the like, and performing crystallization; a method comprising adding water or the like to the reaction mixture and decomposing sulfur trioxide and then, as described above, subjecting the reaction mixture to extraction with a solvent, washing with water or the like, and performing crystallization; and a method comprising adding a poor solvent, such as water, to the reaction mixture, precipitating a crude product, separating the precipitate by filtration, and recrystallizing the filtrate for purification.

The team "comprising" as used herein includes "consisting essentially of" and "consisting of." Further, the present disclosure includes any and all combinations of the components described in the present specification.

Various characteristics (properties, structures, functions, etc.) described in the above embodiments of the present disclosure may be combined in any manner to specify the subject matter included in the present disclosure. That is, this disclosure includes all of the subject matter comprising any combination of the combinable properties described herein.

EXAMPLES

The embodiments of the present disclosure are more specifically explained below with reference to Examples; however, the embodiments are not limited to the Examples shown below.

Production Example 1

100.0 g of 50% fuming sulfuric acid (concentrated sulfuric acid containing 50 mass % sulfur trioxide) (0.62 moles in tams of sulfur trioxide) was placed in a four-necked flask equipped with a stirrer, a cooling tube, a thermometer, and a dropping funnel; and cooled under an ice bath. 20.6 g of 91% paraformaldehyde (0.62 moles in terms of formaldehyde) was slowly added, and the mixture was stirred while the temperature was raised to 70° C. After stirring at 70° C. for 12 hours, the mixture was cooled to 20° C. and the reaction mixture was dropped into ice water. The precipitated solid was separated by filtration, washed with cold water and cold diethyl ether, and then dried in vacuum for 12 hours to obtain 28.9 g (yield: 42%) of a sulfonic acid compound of formula (3) wherein $R^3$ and $R^4$ are all a hydrogen atom. $^1$H-NMR (400 MHz, CD$_3$CN) δ (ppm): 5.30 (s, 4H)

Example 1

7.0 g (0.04 moles) of methanedisulfonic acid, 20 g of sulfolane, and 4.4 g (0.02 moles) of the sulfonic acid compound obtained in Production Example 1 were placed in a four-necked flask equipped with a stirrer, a cooling tube, a thermometer, and a dropping funnel. The temperature was raised to 100° C. and the mixture was stirred at 100° C. for 1 hour. Methylene methanedisulfonate, which is a compound of formula (5) wherein n1 and n2 are 1 and $R^1$, $R^2$, $R^3$, and $R^4$ are a hydrogen atom was produced. The yield of the methylene methanedisulfonate was 47 mol % relative to methanedisulfonic acid. The yield of methylene disulfonate was determined from the peak area value obtained by sampling the reaction mixture and performing HPLC analysis.

Subsequently, the reaction mixture was cooled to 25° C. The viscosity of the reaction mixture was low even at 25° C., and the reaction mixture had excellent flowability.

Further, methylene chloride and water were added to the reaction mixture, and the resulting mixture was subjected to liquid-liquid separation. The obtained organic layer was washed with water and concentrated. The precipitated crystals were separated by filtration and dried at 40° C. at 10 mmHg for 6 hours to obtain 3.2 g of methylene methanedisulfonate, which is a compound of formula (5) wherein n1 and n2 are 1 and $R^1$, $R^2$, $R^3$, and $R^4$ are a hydrogen atom (yield: 42 mol %). $^1$H-NMR analysis confirmed that the obtained crystals were methylene methanedisulfonate.

$^1$H-NMR (400 MHz, CD$_3$CN) δ (ppm): 5.33 (s, 2H), 6.00 (s, 2H).

Example 2

7.0 g (0.04 moles) of methanedisulfonic acid, 20 g of sulfolane, and 17.6 g (0.08 moles) of the sulfuric acid ester compound obtained in Production Example 1 were placed in a four-necked flask equipped with a stirrer, a cooling tube, a thermometer, and a dropping funnel. The temperature was raised to 100° C. and the mixture was stirred at 100° C. for 1 hour. Methylene methanedisulfonate, which is a compound of formula (5) wherein n1 and n2 are 1, and $R^1$, $R^2$, $R^3$, and $R^4$ are a hydrogen atom, was produced. The yield of methylene methanedisulfonate was 89 mol % relative to methanedisulfonic acid. The yield of methylene disulfonate was determined from the peak area value obtained by sampling the reaction mixture and performing HPLC analysis.

Subsequently, the reaction mixture was cooled to 25° C. The viscosity of the reaction mixture was low even at 25° C., and the reaction mixture had excellent flowability.

The above results show that according to the above production method, the reaction can favorably proceed without incurring precipitation of by-products or an increase in the viscosity of the reaction mixture with the progress of the reaction. That is, the production method enables easy and inexpensive production of a cyclic disulfonic acid ester compound without incurring handling problems such as deterioration of stirring during the reaction and an increase in transfer load, thus being suitable for industrial-scale production.

The invention claimed is:

1. A method for producing a cyclic disulfonic acid ester compound, the method comprising reacting at least one sulfonic acid compound with at least one sulfuric acid ester compound, the sulfonic acid compound being selected from the group consisting of:

compounds represented by formula (1):

wherein two Xs are the same or different and represent a hydrogen atom or an alkali metal;
$R^1$ and $R^2$ are the same or different and represent a $C_{1-4}$ alkyl group optionally substituted with one or more halogen atoms or a hydrogen atom;
n1 is an integer of 1 to 4;
when n1 is an integer of 2 to 4, n1 $R^1$s may be the same or different and n1 $R^2$s may be the same or different; and
   compounds represented by formula (2):

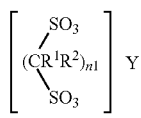

(2)

wherein Y represents an alkaline earth metal, and $R^1$, $R^2$, and n1 are as defined above,
   the sulfuric acid ester compound being selected from the group consisting of:
   compounds represented by formula (3):

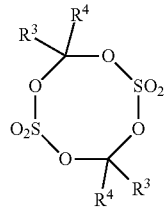

(3)

wherein $R^3$ and $R^4$ are the same or different and represent a $C_{1-4}$ alkyl group optionally substituted with one or more halogen atoms or a hydrogen atom; and compounds represented by formula (4):

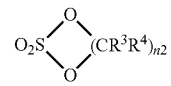

(4)

wherein n2 is an integer of 1 to 4, and $R^3$ and $R^4$ are as defined above, and
   the cyclic disulfonic acid ester compound being represented by formula (5)

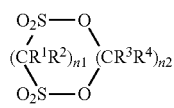

(5)

wherein $R^1$, $R^2$, $R^3$, $R^4$, n1, and n2 are as defined above.

2. The method for producing a cyclic disulfonic acid ester compound according to claim 1, wherein the sulfuric acid ester compound is at least one sulfuric ester compound selected from the group consisting of the compounds represented by formula (3) and the compounds represented by formula (4) wherein n2 is 1.

3. The method for producing a cyclic disulfonic acid ester compound according to claim 1, wherein the sulfonic acid compound is a compound of formula (1) wherein two Xs are both a hydrogen atom.

4. The method for producing a cyclic disulfonic acid ester compound according to claim 2, wherein the sulfonic acid compound is a compound of formula (1) wherein two Xs are both a hydrogen atom.

\* \* \* \* \*